United States Patent [19]

Davies et al.

[11] Patent Number: 5,798,372

[45] Date of Patent: Aug. 25, 1998

[54] METHOD FOR PREVENTING ONSET OF RESTENOSIS AFTER ANGIOPLASTY EMPLOYING A RETINOID

[75] Inventors: Peter A. J. Davies, Houston, Tex.; Roshantha A. Chandraratna, Mission Viejo, Calif.; Claude R. Benedict, Houston, Tex.

[73] Assignees: Allergan, Irvine, Calif.; The University of Texas, Austin, Tex.

[21] Appl. No.: 794,289

[22] Filed: Feb. 3, 1997

Related U.S. Application Data

[63] Continuation of Ser. No. 407,733, Mar. 20, 1995, abandoned.

[51] Int. Cl.⁶ .......................... A61K 31/44; A61K 31/35; A61K 31/19

[52] U.S. Cl. .......................... 514/356; 514/460; 514/568; 514/572

[58] Field of Search .................................. 514/356, 460, 514/568, 572

[56] References Cited

U.S. PATENT DOCUMENTS

| | | | |
|---|---|---|---|
| 4,326,055 | 4/1982 | Loeliger | 542/429 |
| 4,739,098 | 4/1988 | Chandraratna | 560/8 |
| 5,116,864 | 5/1992 | March et al. | 514/455 |
| 5,140,012 | 8/1992 | McGovern et al. | 514/19 |
| 5,166,143 | 11/1992 | Ondetti et al. | 514/89 |
| 5,213,561 | 5/1993 | Weinstein et al. | 600/7 |
| 5,324,840 | 6/1994 | Chandraratna | 546/318 |
| 5,326,898 | 7/1994 | Chandraatra | 560/17 |

FOREIGN PATENT DOCUMENTS

| | | |
|---|---|---|
| 0176034 | 4/1986 | European Pat. Off. . |
| 0 379 367 | 7/1990 | European Pat. Off. . |
| 3434946 | 4/1986 | Germany . |
| 93/25530 | 12/1993 | WIPO . |
| 94/17796 | 8/1994 | WIPO . |

OTHER PUBLICATIONS

CA 109:55005, Chandraratna, Apr. 1988.
CA 116:227585, Chien et al, 1992.
CA 117:97170, McCarthy et al, 1991.
Serruys et al; Incidence of restenosis after successful coronary angioplasty: a time–related phenomenon; Therapy and Prevention–Coronary Angioplasty; vol. 77, No. 2, pp. 361–371, Feb. 1988.

Willerson et al; Frequency and severity of cyclic flow alternations and platelet aggregation predict the severity of neoointimal proliferation following experimental coronary stenosis and endothelial injury; Proc. Natl. Acad. Sci.; vol. 88, pp. 10624–10628, Dec. 1991; Medical Sciences.

Pakala et al, "All Trans–retinoic acid and its derivatives inhibit serotonin–induced vascular smooth cell proliferation", *Journal of the American College of Cardiology*, vol. 0 (spec. issue), 1995, pp. 83A–84A, Abstract No. 713-2.

Lyons et al, "Effect of oral 13–cis–retinoic acid on serum lipids", *British Journal of Dermatology*, vol. 107, 1982, pp. 591–595.

Kato et al, "Down–regulation in the production of matrix metalloproteinase 1 by human aortic intimal smooth muscle cells", *Biochem. Mol. Biol. Int.*, vol. 31, No. 2, Oct. 1993, pp. 239–248.

Hayashi et al, "Modulations of elastin expression and cell proliferation by retinoids in cultured vascular smooth muscle cells", *J. Biochem.*, vol. 117, No. 1, 1995, pp. 132–136.

Liu et al, "Systemic pharmacokinetics of acetylenic retinoids in rats", *Drug Metab. Dispos.*, vol. 18, No. 6, 1990, pp. 1071–1077.

Barstad et al, "Retinoic acid reduces induction of monocyte tissue factor and tissue factor/factor VIIa–dependent arterial thrombus formation", *Blood*, vol. 86, No. 1, 1 Jul. 1995, pp. 212–218.

Chemical Abstracts, vol. 111, No. 3, 17 Jul. 1989, Abstract No. 23742, see Abstract & J. Med. Chem. vol. 32, No. 5, 1989 Kagechika et al, "Retinobenzoic acids".

*Primary Examiner*—Kimberly Jordan
*Attorney, Agent, or Firm*—Robert J. Baran; Martin A. Voet; Howard R. Lambert

[57] ABSTRACT

A method is provided for preventing or reducing the risk of restenosis following angioplasty by administering a retinoid, such as an RAR-selective retinoid, e.g. the compound of the formula:

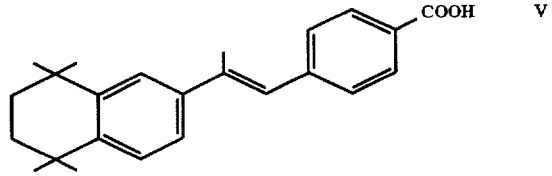

9 Claims, 1 Drawing Sheet

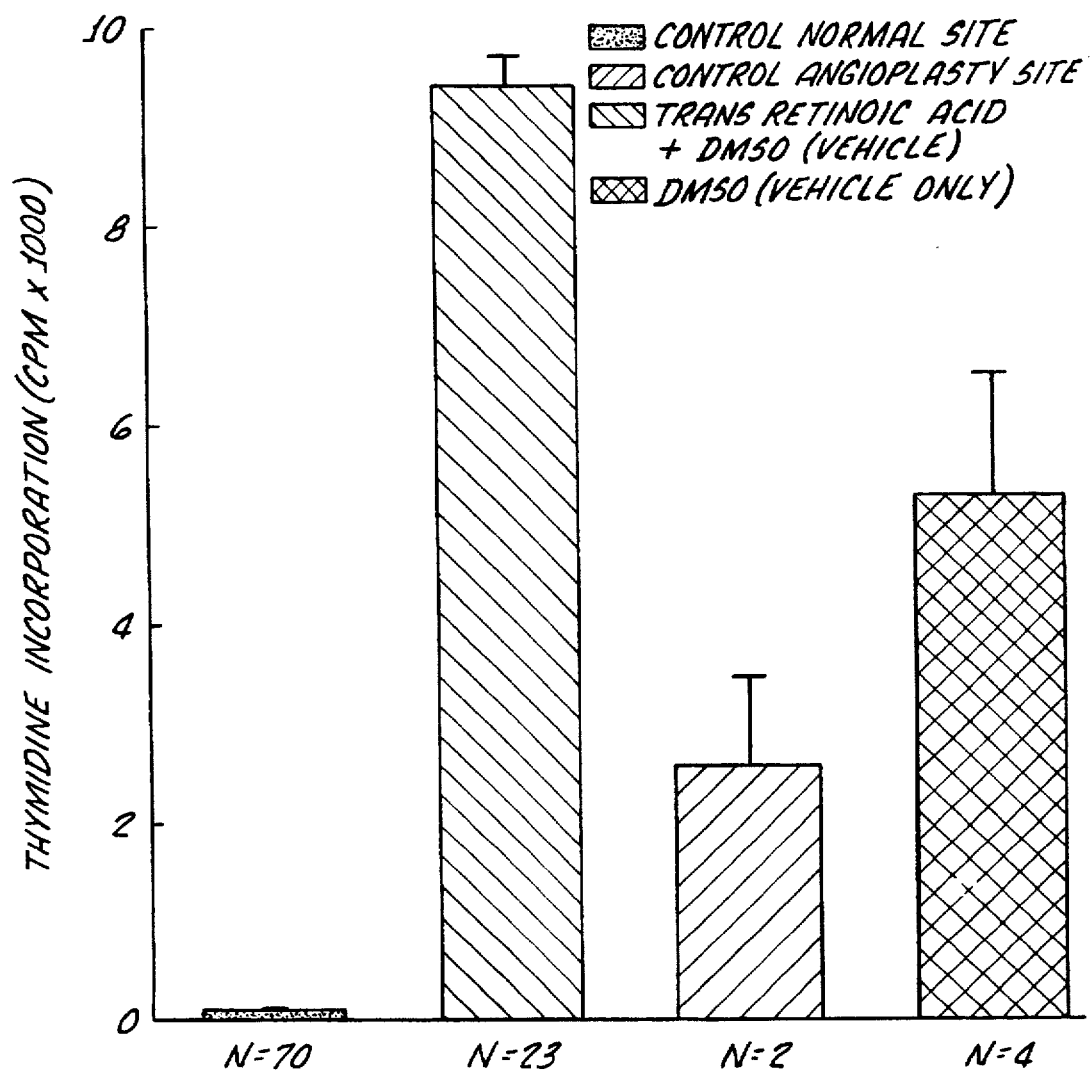

METHOD FOR PREVENTING ONSET OF RESTENOSIS AFTER ANGIOPLASTY EMPLOYING A RETINOID

This application is a continuation of application Ser. No. 08/407,733 filed on Mar. 20, 1995, now abandoned.

FIELD OF THE INVENTION

The present invention relates to a method for preventing onset of restenosis after angioplasty by administering a retinoid, and which is preferably an agonist that is selective at the RAR receptor, i.e. a retinoid having greater selectivity for the RAR receptor than the RXR receptor, or a pan agonist, i.e. a retinoid that may activate either the RAR or RXR receptor.

BACKGROUND OF THE INVENTION

Percutaneous transluminal angioplasty (PTA), defined as any percutaneous transluminal method of decreasing stenosis within a blood vessel, whether caused by the existence of an atheromatous plaque, thrombosis, embolus, and/or mineral deposit, by any of a number of means such as balloon dilation, thermal ablation, laser atherectomy, mechanical shaving, extraction or ultrasonic pulverization, hereinafter referred to as angioplasty, is widely used in the treatment of occlusive vascular disease. However, it has been found that restenosis frequently occurs, and in the case of coronary angioplasty, restenosis occurs in about a third of cases within 6 months of the procedure.

Angiotensin converting enzyme (ACE) inhibitors or the physiologically tolerable salts thereof have been used in the treatment of atherosclerosis, thrombosis and/or peripheral vascular disease in mammals. It has been disclosed that, because ACE is predominantly localized in the luminal plasma membrane of the endothelial cell, ACE inhibitors can interfere in platelet-endothelium interaction. In addition, ACE inhibition potentiates the action of bradykinin (a strong stimulator of prostacyclin release from endothelial cells) by inhibiting its degradation and ACE inhibitors, consequently, have an inhibitory effect on platelet aggregation (See U.S. Pat. Nos. 5,140,012 and 5,166,143). In large scale clinical trials, ACE inhibitors have failed to demonstrate a beneficial effect in preventing restenosis following angioplasty.

Other methods for preventing restenosis after angioplasty include combining photoactivatable psoralen and ultraviolet radiation, as set forth in U.S. Pat. No. 5,116,864, and radiation from a source of radioactivity, as set forth in U.S. Pat. No. 5,213,561.

Recently, a gene has been discovered, that is present in certain families resident in Limone, Italy, which codes for a protein that may have the function of preventing the build-up of fatty deposits that clog the arteries and may be especially effective in preventing the reclogging of arteries that occurs after a blocked vessel has been cleared with balloon angioplasty surgery.

However, to date, none of the present methods for preventing restenosis are suitable in every aspect. Therefore, the search for methods for preventing the onset of restenosis after angioplasty continues.

DESCRIPTION OF THE DRAWING FIGURE

The FIGURE shows the effect of treatment with trans retinoic acid on rabbit iliac artery angioplasty.

DESCRIPTION OF THE INVENTION

In accordance with the present invention, a method is provided for preventing onset of or reducing risk of restenosis following angioplasty, wherein a therapeutically effective amount of a retinoid is administered systemically, such as orally or parenterally.

The retinoid may be administered prior to, during and/or after the angioplasty procedure.

It is believed that the retinoid reduces the incidence of restenosis by preventing cell proliferation.

The term "restenosis" as employed herein is as defined by Serruys, P. W., et al, "Incidence of restenosis after successful coronary angioplasty; a time related phenomenon. A quantitative angiographic study in 342-consecutive patients at 1, 2, 3, and 4 months, " Circulation 1988; 7:361–71.

In preferred embodiments where the patient to be treated in accordance with the present invention is normotensive, the retinoid will preferably be administered in amounts below that which causes side effects.

The selective RAR agonists useful in the method of the present invention include compounds of the following formulae:

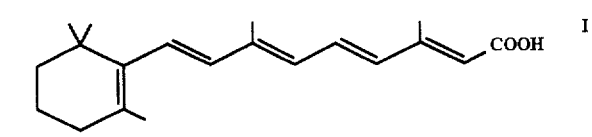

AGN 100335 (ATRA): (E)-3,7-dimethyl-9-(2,6,6-trimethyl-1-cyclohexen-1-yl)-2, 4,6,8-nonatetraenoic acid

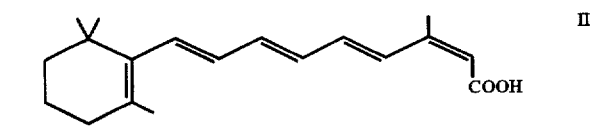

AGN 190013 (13-cis-RA) : (2Z,4E,6E,8E)-3, 7-dimethyl-9-(2,6,6-trimethyl-1-cyclohexen-1-yl)-2,4, 6,8-nonatetraenoic acid

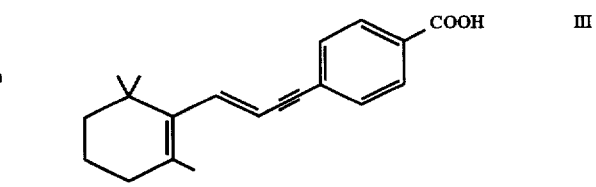

AGN 190121 (E)-4-[4-(2,6,6-trimethyl-1-cyclohexen-1-yl)but-2-en-1-ynyl] benzoic acid

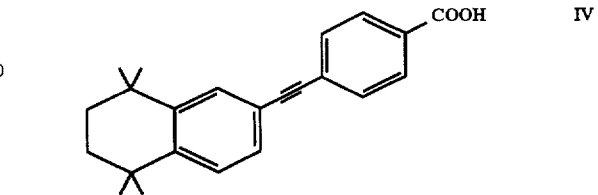

AGN 190205 4-[2-(5,6,7,8-tetrahydro-5,5,8, 8-tetramethyl-2-naphthalenyl)ethynyl] benzoic acid

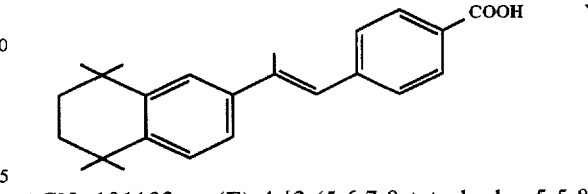

AGN 191183 : (E)-4-[2-(5,6,7,8-tetrahydro-5,5,8, 8-tetramethyl-2-naphthalenyl)-1-propen-1-yl] benzoic acid

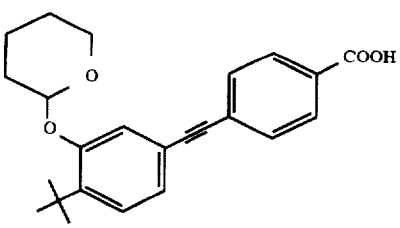

AGN 192326 : 4-[2-(3-(2-tetrahydropyranyl)oxy)-(4-(1,1-dimethylethyl)phenyl)ethynyl]benzoic acid

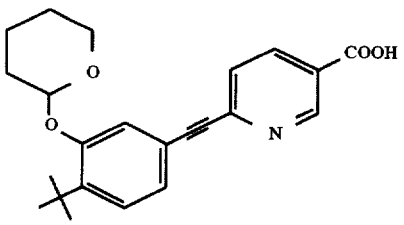

AGN 192327 : 6-[2-(3-(2-tetrahydropyranyl)oxy)-(4-(1,1-dimethylethyl)phenyl)ethynyl]-3-nicotinic acid The panagonists useful in the method of the present invention include compounds of the following formulae:

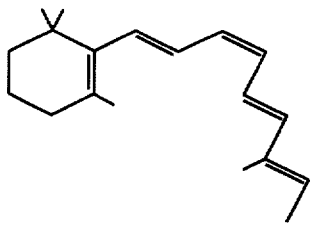

AGN 192013 (9-cis RA) (2E,4E,6Z,8E)-3,7-dimethyl-9-(2,6,6-trimethyl-1-cyclohexen-1-yl)-2,4,6,8-nonatetraenoic acid

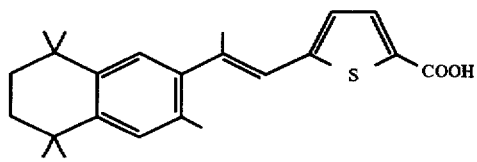

AGN 191659 : (E)-5-[2-(5,6,7,8-tetrahydro-3,5,5,8,8-pentamethyl-2-naphthalenyl)-1-propen-1-yl] thiophene-2-carboxylic acid Examples of these retinoids which may be employed in the method of this invention may be found in U.S. Pat. Nos. 4,739,098 and 4,326,055; European Patent Application 176034A, published April 2, 1986 and PCT Patent Applications WO 93/25530 and WO 94/17796.

Other of the retinoids described above may be prepared according to the following reaction scheme:

Ethyl 4-[2-[[2-t-butyl-1-(2-tetrahydropyranoxy)]-4-phenyl]ethyn-1-yl] benzoate (Compound 1)

To a 100 ml 3-necked round bottom flask (fitted with a glass stopper, reflux condenser, and a rubber septum) was added 25 ml of diethylamine (distilled over solid KOH). The solvent was degassed with a vigorous stream of argon gas for several minutes. To this solution was added 2.67 g (10.3 mmol) of 2-[[2-t-butyl-1-(2-tetrahydropyranoxy)]-4-phenyl] acetylene (Compound N) dissolved in 10 ml of diethylamine, 0.39 g (2.1 mmol) of cuprous iodide (ground to a powder), and 2.72 g (9.8 mmol) of ethyl 4-iodobenzoate (Compound A) dissolved in 5 ml of diethylamine. The resultant yellow solution was degassed for 10 minutes after which 1.67 g (2.4 mmol) of bis(triphenyl)phosphine palladium (II) chloride was added. The solution was cooled to 0° C. and stirred at 0° C. for 30 minutes (the initial 5 minutes of stirring were performed with argon purge). The reaction mixture was allowed to warm to room temperature and then stirred overnight. A salt formed against the walls of the flask. The reaction mixture was filtered through celite, washed with 500 ml of ethyl ether and the celite plug discarded. The filtrate was washed with 4×200 ml portions of water and 150 ml of brine solution, dried over $K_2CO_3$, filtered and concentrated in vacuo to yield a yellow foam. Purification by flash chromatography (silica, 5% ethyl acetate in hexane) followed by recrystallization (methanol) yielded the title compound as beige needles.

4-[2-[[2-t-butyl-1-(2-tetrahydropyranoxy)]-4-phenyl]ethyn-1-yl] benzoic acid (Compound 2)

To a solution of 2.00 g (4.9 mmol) of ethyl 4-[2-[[2-t-butyl-1-(2-tetrahydropyranoxy)] -4-phenyl]ethyn-1-yl] benzoate (Compound 1) in 80 ml of tetrahydrofuran was added 19.7 ml (9.8 mmol) of LiOH (0.5M aqueous solution). The yellow, homogeneous solution was allowed to stir at room temperature for 19 hours. The reaction mixture was concentrate in vacuo, partitioned between 100 ml of water and 60 ml of hexane and the layers were separated. The aqueous phase was diluted with 200 ml of ethyl ether, cooled to 0° C. and acidified with 1N sulfuric acid to an approximate pH of 4–5. The layers were separated and the aqueous layer was discarded. The organic phase was washed once with brine solution, dried over $MgSO_4$, filtered and concentrated in vacuo to yield a white solid. The solid was recrystallized (acetonitrile) to give the title compound as fine, white needles.

Ethyl 6-[2-[[2-t-butyl-1-(2-tetrahydropyranoxy)]-4-phenyl]ethyn-1-yl] nicotinate (Compound 3)

Using the same general procedure as for the preparation of ethyl 4-[2-[[2-t-butyl-1-(2-tetrahydropyranoxy)]-4-phenyl]ethyn-1-yl] benzoate (Compound 1), but instead using 2.84 g (11.0 mmol) of 2-[[2-t-butyl-1-(2-tetrahydropyranoxy)]4-phenyl] acetylene (Compound N), 0.38 g (2.0 mmol) of cuprous iodide (ground to a powder), 2.76 g (10.0 mmol) of ethyl 6-iodonicotinate (Compound C), 1.61 g (2.3 mmol) of bis(triphenyl)phosphine palladium (II) chloride and 50 ml of diethylamine gave a foamy yellowish-red solid. Purification by flash chromatography (silica, 5% ethyl acetate in hexane) followed by recrystallization (methanol) yielded the title compound as yellow crystals.

6-[2-[[2-t-butyl-1-(2-tetrahydropyranoxy)]-4phenyl] ethyn-1-yl ] nicotinic acid (Compound 4)

Using the same general procedure as for the preparation of 4-[2[[2-t-butyl-1-(2-tetrahydropyranoxy)]-4-phenyl] ethyn-1-yl] benzoic acid (Compound 2), but instead using 1.90 g (4.7 mmol) of ethyl 6-[2-[[2-t-butyl-1-(2-tetrahydropyranoxy)]-4-phenyl]ethyn-1-yl] nicotinate (Compound 3), 18.7 ml (9.3 mmol) of LiOH (0.5M aqueous solution) and 80 ml of tetrahydrofuran gave a yellow-white solid. The solid was recrystallized (acetonitrile) to give the title compound as fine, yellow, needle-like crystals.

Ethyl 6-[2-[[2-t-butyl-1-(2-tetrahydropyranoxy)]-5-phenyl]ethyn-1-yl] nicotinate (Compound 5)

Using the same general procedure as for the preparation of ethyl 4-[2-[[2-t-butyl-1-(2-tetrahydropyranoxy)]-4- phenyl]ethyn-1-yl] benzoate (Compound 1), but instead using 2.21 g (8.6 mmol) of 2-[[2-t-butyl-1-(2-tetrahydropranoxy) ]-5-phenyl]acetylene (Compound 0), 0.45 g (2.4 mmol) of cuprous iodide (ground to a powder), 2.15 g (7.8 mmol) of ethyl 6-iodonicotinate (Compound C), 1.89 g (2.7 mmol) of bis(triphenyl) phosphine palladium (II) chloride and 45 ml of diethylamine gave an orange foam. Purification by flash chromatography (pre-absorbed onto silica with chloroform, eluted with 10% ethyl acetate in hexane) followed by recrystallization (methanol) yielded the title compound as bright yellow, needles.

Ethyl 4-[2-[[2-t-butyl-1-(2-tetrahydropyranoxy)]1-5-phenyl]ethyn-1-yl] benzoate (Compound 6)

Using the same general procedure as for the preparation of ethyl 4-[2-[[2-t-butyl-1-(2-tetrahydropyranoxy)]-4-phenyl]ethyn-1-yl] benzoate (Compound 1), but instead using 3.30 g (12.8 mmol) of 2-[[2-t-butyl-1-(2-tetrahydropyranoxy) ]-5-phenyl]acetylene (Compound 0), 0.44 g (2.3 mmol) of cuprous iodide (ground to a powder), 3.20 g (11.6 mmol) of ethyl 4-iodobenzoate (Compound A), 1.87 g (2.7 mmol) of bis(triphenyl)phosphine palladium (II) chloride and 50 ml of diethylamine produced an orange foam. Purification by flash chromatography (preabsorbed onto silica with chloroform, eluted with 5% ethyl acetate in hexane) followed by recrystallization (methanol) yielded the title compound as light brown clusters.

4-[2-[[2-t-butyl-1-(2-tetrahydropyranoxy)]-5-phenyl] ethyn-1-yl] benzoic acid (Compound 7)

Using the same general procedure as for the preparation of 4-[2-[[2-t-butyl-1-(2-tetrahydropyranoxy)]-4-phenyl] ethyn-1-yl] benzoic acid (Compound 2), but instead using 2.01 g (5.1 mmol) of ethyl 4-[2-[[2-t-butyl-1-(2-tetrahydropyranoxy)]-5-phenyl]ethyn-1-yl] benzoate (Compound 6),10.5 ml (10.5 mmol) of LiOH (1M aqueous solution) and 44 ml of tetrahydrofuran (THEF), stirred at room temperature for 48 hours and then refluxed overnight produced a white solid. Purification by flash chromatography (silica, 10% ethyl acetate in hexane followed by 15% methanol in dichloromethane) yielded the title compound as an off-white solid.

6[2-[[2-t-butyl-1-(2-tetrahydropyranoxy)]-5-phenyl] ethyn-1-yl] nicotinic acid (Compound 8)

Using the same general procedure as for the preparation of 4-[2-[[2-t-butyl-1-(2-tetrahydropyranoxy)]-4-phenyl] ethyn-1-yl] benzoic acid (Compound 2), but instead using 1.50 g (3.8 mmol) of ethyl 6-[2-[[2-t-butyl-1-(2-tetrahydropyranoxy)]-5-phenyl]ethyn-1-yl] nicotinate (Compound 5), 8.0 ml (8.0 mmol) of LiOH (1M aqueous solution) and 32 ml of tetrahydrofuran produced a yellow solid. The solid was recrystallized (acetonitrile) to give the title compound as bright yellow crystals.

Preferred are those retinoids which are selective RAR receptor agonists or pan agonists. Most preferred are the retinoids that are RAR receptor agonists.

The above-mentioned patents and patent applications are incorporated herein by reference.

In carrying out the method of the present invention, the retinoid is administered to mammalian species, such as dogs, cats, humans, etc., prior to during and/or after the angioplasty procedure, and as such may be incorporated in a conventional systemic dosage form, such as a tablet, capsule, elixir or injectable. In the above dosage forms the retinoid will be combined with a pharmaceutically-acceptable carrier including the necessary carrier materials, excipient, lubricant, buffer, antibacterial, bulking agent (such as mannitol), anti-oxidants (ascorbic acid of sodium bisulfite) or the like. Oral dosage forms are preferred, although parental forms are quite satisfactory as well.

Thus, for oral administration, a satisfactory result may be obtained employing the retinoid in an amount within the range of from about 0.01 mg/kg to about 100 mg/kg and preferably from about 0.1 mg/kg to about 5 mg/kg.

A preferred oral dosage form, such as tablets or capsules, will contain a retinoid in an amount of from about 0.1 to about 500 mg, preferably from about 2 to about 50 mg, and more preferably from about 5 to about 25 mg.

For parenteral administration, the retinoid will be employed in an amount within the range of from about 0.005 mg/kg to about 10 mg/kg and preferably from about 0.005 mg/kg to about 1.5 mg/kg.

The compositions described above may be administered in the dosage forms as described above in single or divided doses of one to four times daily. It may be advisable to start a patient on a low dose and work up gradually to a high dose.

Tablets of various sizes can be prepared, e.g. of abut 2 to 2000 mg in total weight, containing one or both of the active substances in the ranges described above, with the remainder being a pharmaceutically-acceptable of other materials according to accepted pharmaceutical practice. These tablets can, of course, be scored to provide for fractional doses. Gelatin capsules can be similarly formulated.

Liquid formulations can also be prepared by dissolving or suspending one or the combination of the active substances in a conventional liquid vehicle acceptable for pharmaceutical administration so as to provide the desired dosage in one to four teaspoonfuls.

Such dosage forms can be administered to the patient on a regimen of one to four doses per day.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin, an excipient such as dicalcium phosphate or cellulose, a disintegrating agent such as corn starch, potato starch, alginic acid or the like, a lubricant such as stearic acid or magnesium stearate, a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Some of the active substances described above form commonly known, pharmaceutically-acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for 4 weeks to 6 months or longer, beginning at the time of the angioplasty procedure. Sustained release forms of such formulations which may provide such amounts biweekly, weekly, monthly and the like may also be employed. A dosing period of at least one to two weeks are required to achieve minimal benefit.

The following Examples represent preferred embodiments of the present invention.

As will be further demonstrated below, the retinoids of choice for practicing the method of this invention are RAR selective agonists or pan agonists, and more preferably, RAR agonists. It is well known in the art, how to determine whether retinoids are RAR agonists, RXR agonists or pan agonists. It particular, refer to PCT Patent Application WO 93/25530, which was published on 23 Dec. 1993, and is hereby incorporated by reference, for a description of assays for determining RAR and RXR agonist activity. (Of course, pan agonists show agonist activity at both the RAR and RXR receptor.)

DETAILED DESCRIPTION OF THE INVENTION

For the purposes of this invention a RAR selective agonist preferably will have a ratio of activity at the RAR vs the RXR receptor of at least 5, and more preferably about at least 10. A pan agonist will have activity at both of the RAR and RXR receptor, e.g. similar potency at the RAR and RXR receptor.

An important role for serotonin (5HT) and thromboxane $A_2$ (TxA$_2$) in contributing to neointimal proliferation in an in vivo awake dog model of coronary arterial injury has been identified (See "Frequency and severity of cyclic flow alternations and platelet aggregation predict the severity of neointimal proliferation following experimental coronary stenosis and endothelial injury", Willerson J T, et al Proc. Natl. Acad. Sci USA 88:10624–10628, 1991). It has been established that 5HT can induce mitogenesis by promoting DNA synthesis ($^3$H-thymidine incorporation) in aortic endothelial and smooth muscle cells. It has also been demonstrated that acidic fibroblast growth factor (β-FGF) and platelet derived growth factor (PDGF) are potent mitogens for vascular endothelial and smooth muscle cells and may have important synergism with the mitogenic effect of 5HT on these cells. Therefore, the arterial endothelial and smooth muscle cell culture system described below is an ideal system to rapidly examine whether retinoids, have important antiproliferative properties.

The effect of 1% serum on DNA synthesis by endothelial or smooth muscle cells using $^3$H-thymidine incorporation was measured. For measuring the effectiveness of retinoids in inhibiting endothelial or smooth muscle cell proliferation induced by certain mitogens, i.e., serotonin or β-FGF the indicated concentrations were added to the media instead of 1% serum. Primary cells isolated from canine aorta were used for these studies. Unlike the typical cell lines (e.g. NIH 3T3 cells, etc.) 6–7 weeks are required to isolate and grow these primary cells in sufficient number to perform a single experiment. For the following studies, the primary cells (passages 2–4) were plated on 35×10 mm tissue culture dishes in 10% fetal bovine serum (FBS) and incubated. After 72 hours of growth the medias was replaced with 0.1% FBS for synchronization and incubated for additional 72 hours. Then 1% serum was added and incubated for 20 hours followed by the addition of 1µCi of $^3$H-thymidine. Four hours after the addition of 3H-thymidine the DNA was precipitated and the amount of $^3$H-thymidine incorporated was measured. This value is reported as the serum or serotonin or β-FGF stimulated value for cellular proliferation and is expressed as a percentage of baseline $^3$H-thymidine incorporation.

To examine the antiproliferative effect of retinoids, they were dissolved in 100% ethanol and then added at the indicated final concentrations. The compounds were added at the time of adding 1% serum or serotonin or β-FGF to stimulate the cells. (The maximal final concentration of ethanol in culture media was 1% which is non-cytotoxic to endothelial or smooth muscle cells). After 20 hours of incubation with retinoids and 1% serum or serotonin or β-FGF, the $^3$H-thymidine incorporation was measured.

As shown in the Table 2 below, the rank order potency on smooth muscle cells appears to be AGN 191659= 191183>AGN 192327>AGN 191985>AGN 192326. For endothelial cells the order of potency is AGN 192013>AGN 190205=AGN 191183.

The results of testing the effect of AGN 191183 on smooth muscle and endothelial cell growth is reported in Table 1, below. In this experimental dosages ranging between 0.01 and 100 µM were evaluated for the effect of AGN 191183 on cell growth. It is found by plotting the percent cell growth versus the dose that the concentration at which cell proliferation is inhibited by 50% (ED50) is 0.03 µM and 6.15 µM, for smooth muscle and endothelial cells, respectively.

TABLE 1

EFFECT OF AGN #191183 ON SERUM INDUCED CELL PROLIFERATION

| DOSE (µM) | % SMOOTH MUSCLE | % ENDOTHELIAL |
|---|---|---|
| 0 | 100* | 100** |
| Stimulated | 725 ± 170 | 1246 ± 91 |
| 0.01 | 376 ± 17 | 1349 ± 24 |
| 0.05 | 348 ± 95 | 1046 ± 71 |
| 0.1 | 219 ± 22 | 959 ± 115 |
| 0.5 | 205 ± 17 | 840 ± 108 |
| 1 | 185 ± 10 | 815 ± 171 |
| 5 | 182 ± 3 | 686 ± 40 |
| 10 | 126 ± 18 | 406 ± 32 |
| 50 | 137 ± 25 | 17 ± 2 |
| 100 | 77 ± 28 | 9.3 ± 2.3 |

*100% = 2108 ± 165 cpm/10$^6$ cells
**100% = 1739 ± 71 cpm/10$^6$ cells

The other retinoids, disclosed above, were also tested for their effect on smooth muscle and endothelial cell growth at the same dosages as for AGN 191183. Table 2 reports the ED$_{50}$ for each of these retinoids.

TABLE 2

CONCENTRATION OF RETINOIDS AT WHICH SMOOTH MUSCLE CELL AND ENDOTHELIAL CELL PROLIFERATION IS INHIBITED BY 50%

| COMPOUND (AGN) | ED$_{50}$ FOR SMOOTH MUSCLE CELLS (µM) | ED$_{50}$ FOR ENDOTHELIAL CELL (µM) | SELECTIVITY |
|---|---|---|---|
| 100335 | 35.8 | 28 | RAR |
| 190013 | 7.4 | 31.5 | RAR |
| 192013 | >100 | 2.25 | PAN AGONIST |
| 190121 | 46 | 23 | RAR |
| 190205 | 8.95 | 6.8 | RAR |
| 191183 | 0.03 | 6.15 | RAR |
| 191659 | 0.038 | 39 | PAN AGONIST |

TABLE 2-continued

CONCENTRATION OF RETINOIDS AT WHICH SMOOTH MUSCLE CELL AND ENDOTHELIAL CELL PROLIFERATION IS INHIBITED BY 50%

| COMPOUND (AGN) | $ED_{50}$ FOR SMOOTH MUSCLE CELLS (μM) | $ED_{50}$ FOR ENDOTHELIAL CELL (μM) | SELECTIVITY |
|---|---|---|---|
| 191701 | 18 | 28.5 | RXR |
| 191985 | 6.25 | 75.5 | RXR |
| 192326 | 6.5 | 16.5 | RAR |
| 192327 | 4 | 29 | RAR |

It is clear from the results that the RAR selective retinoids are generally more effective than the pan agonists which are more effective than RXR selective retinoids. In particular, AGN 191183 is the most effective retinoid for inhibiting the growth of both smooth muscle and endothelial cells.

Certain of the retinoids were then tested for mitogen-induced cellular proliferation, utilizing serotonin (5HT) and β-FGF as such mitogens. In this testing, as reported in Table 3, below, the same dosages were evaluated for their effect on mitogen-induced cellular proliferation (The results are reported as ED50 and compared to the $ED_{50}$ for serum-induced smooth muscle and endothelial cell growth).

TABLE 3

COMPARATIVE CONCENTRATIONS OF RETINOIDS AT WHICH SMOOTH MUSCLE CELL AND ENDOTHELIAL CELL PROLIFERATION IS INHIBITED BY 50%

| COMPOUND AGN | $ED_{50}$ FOR SMOOTH MUSCLE CELLS (μM) | | | $ED_{50}$ FOR ENDOTHELIAL Cells (μM) | | | RETINOID SELECTIVITY |
|---|---|---|---|---|---|---|---|
| | Serum | Serotonin | β-FGF | Serum | Serotonin | β-FGF | |
| 100335 | 35.8 | 0.047 | >100 | 28 | 0.025 | 0.009 | RAR |
| 190013 | 7.4 | 5 | >100 | 31.5 | 0.0092 | 0.009 | RAR |
| 192013 | >100 | 0.41 | >100 | 2.25 | 0.16 | 26.5 | PANAGONIST |

It might be anticipated that 1% serum would be the most potent mitogen for both the cell types and the concentration of retinoids that are required to inhibit the serotonin or β-FGF-induced cellular proliferation would be less. For endothelial cells this appears to be partially true. However, for smooth muscle cells the retinoids examined do not block the β-FGF-induced cellular proliferation.

There has been interest in attempting to reduce the incidence of restenosis by minimizing the trauma of angioplasty. Studies with laser angioplasty have demonstrated a direct relationship between the degree of thermal injury and the amount of neontimal proliferation produced. However, a similar relationship between the degree of injury and restenosis has not been documented with conventional balloon angioplasty. In order to better characterize the time course and degree of cellular proliferation resulting from vascular injury, the effect of retinoids on the in vivo incorporation of 3H-thymidine in a rabbit model of arterial injury was studied. Varying degrees of injury were produced including both simple de-endothelialization of the intima as well as stretch injury of the vessel by conventional angioplasty. The effect of AGN 100335 (trans retinoic acid) to inhibit cellular proliferation induced by balloon angioplasty was studied.

3.0–3.5 kg male, New Zealand white rabbits underwent standardized femoral artery injury. Arterial access was obtained through the right carotid artery which was ligated after the procedure. Heparin (100 U/kg IV) was given once arterial access was obtained. Injury was accomplished by the following method:

1. A 2.5 mm by 2 cm balloon catheter inflated 3 times to 8 atmospheres (ATM) for 30 seconds (n=71).

Positioning of the balloon catheter was standardized by placing the midpoint of the balloon at 40% of the distance between the femoral head and knee, as seen under fluoroscopy.

At various time points after injury (1, 1.25, 1.5, 2, 3, 4, 5, 6, 7, 8, 9, 10, 12,14, 20 and 28 days), 0.25 μCi/kg of ³H-thymidine was injected through the medial ear vein and flushed with 10 cc of saline. The ³H-thymidine was injected one hour prior to the time of sacrifice. The animals were sacrificed with a 2 cc intracardiac injection of euthanasia solution. Arterial specimens were harvested by excision from the inguinal ligament to the distal bifurcation of the femoral artery. Specimens were stored at –40° C. until time of assay.

Arterial specimens were then thawed and stripped of all adventitia. The tissue was digested in 3 ml of 0.5 N NaOH at 100° C. for one hour. Nucleic acids were precipitated by cooling the digested specimens in an ice bath and adding 1 cc of 40% trichloro acetic acid (TCA). The precipitate was collected by centrifugation at 6,300 g for 10 minutes. The supernatant was decanted and the tubes were inverted to allow any remaining supernatant to drain. The precipitate was redigested in 200 μl of 0.5N NaOH and pipetted into scintillation vials. The samples were neutralized with 0.5N HCl and counted using multisol scintillation fluid.

Using the above described model of angioplasty induced restenosis it was determined whether chronic treatment with all trans retinoic acid can attenuate the cellular proliferation of the site of vascular injury. The following protocol was used for this study:

Day 1: 10 cc of blood was drawn and serum frozen as baseline sample. 10 mg/kg of all trans retinoic acid dissolved in dimethylsulfoxide (DMSO) (10 mg/ml) and then diluted 1:1 with soybean oil was administered intraperitoneally (IP)

Days 2–6: The above mixture was injected daily (6 days of pretreatment prior to injury)

Day 7: Rabbits underwent balloon angioplasty

Days 7–9: Rabbits continued to receive daily IP injection of retinoic acid

Day 10: Rabbits received ³H-thymidine as described previously to assess the DNA synthesis at the site of vascular injury and then sacrificed one hour later From this in-vivo testing it was concluded that retinoic acid at a dose of 10 mg/kg appeared to inhibit the development of cellular proliferation following angioplasty. However, the number of animals available for analysis were very small. Also, 2 out of 4 animals receiving retinoic acid died before the study was completed. This effect may be a result of toxicity due to large doses of retinoic acid. It is believed that lower doses may prevent this effect. These results are reported in FIG. 35.

While particular embodiments of the invention have been described, it will be understood, of course , that the invention is not limited thereto since many obvious modifications can be made, and it is intended to include within this invention any such modification as will fall within the scope of the appended claims.

Having now described the invention, we claim:

1. A method for preventing restenosis following angioplasty, which comprises administering to a mammalian specie in need thereof of an effective amount of a retinoid wherein said retinoid is a selective RAR receptor agonist or a pan agonist.

2. The method of claim 1 wherein said retinoid is a selective RAR receptor agonist.

3. The method of claim 2 wherein said selective RAR receptor agonist has a ratio of activity at the RAR receptor versus the RXR receptor of at least 10.

4. The method of claim 1 wherein the retinoid is administered prior to angioplasty.

5. The method of claim 1 wherein the retinoid is administered during angioplasty.

6. The method of claim 1 wherein the retinoid is administered after angioplasty.

7. The method of claim 1 wherein said retinoid is administered in single or divided dose of from about 0.1 to about 500 mg/one to four times daily.

8. The method of claim 1 wherein the retinoid is selected from the group consisting of compounds represented by the formulae:

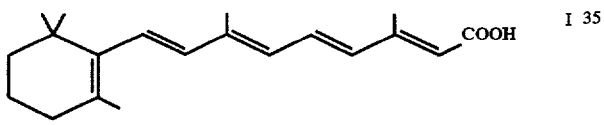

I

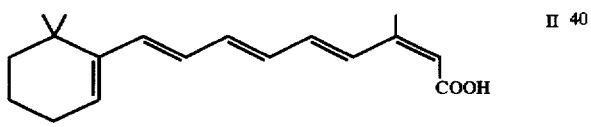

II

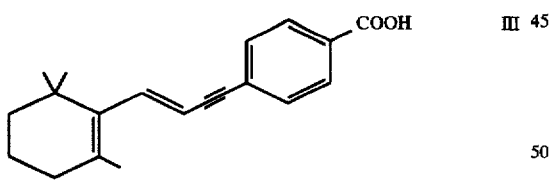

III

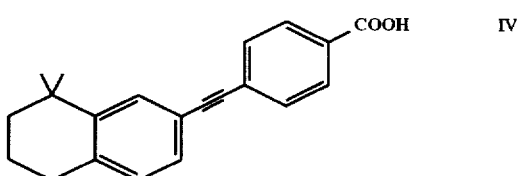

IV

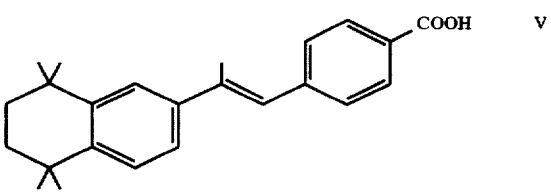

V

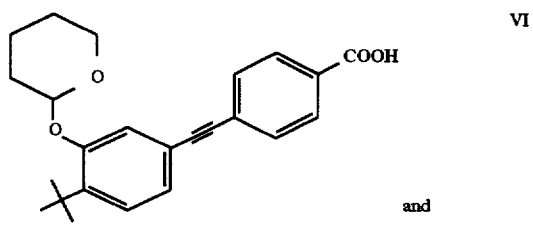

VI and

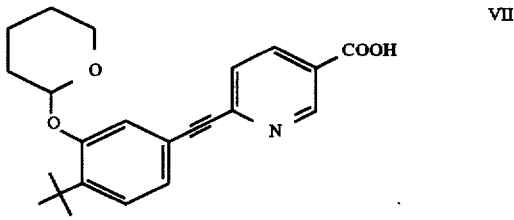

VII

9. The method of claim 8 wherein said retinoid is

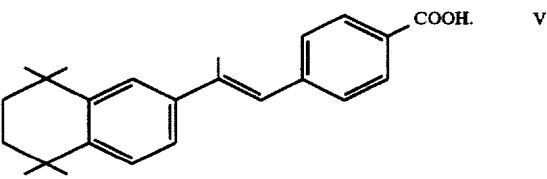

V

* * * * *

UNITED STATES PATENT AND TRADEMARK OFFICE
CERTIFICATE OF CORRECTION

PATENT NO. : 5,798,372
DATED : August 25, 1998
INVENTOR(S) : Davies et al

It is certified that error appears in the above-indentified patent and that said Letters Patent is hereby corrected as shown below:

Column 5, line 12; delete "1-5-" and insert in place thereof -- -5- --

Column 5, line 38; delete "THEF" and insert in place thereof --THF--

Column 6, line 26; after "acceptable" insert --carrier--

Column 8, line 26; delete "ED50" and insert in place thereof --$ED_{50}$--

Column 9, line 26; delete "ED50 (first occurrence)" and insert in place thereof --$ED_{50}$--

Signed and Sealed this

Twelfth Day of January, 1999

Attest:

Attesting Officer

Acting Commissioner of Patents and Trademarks